US008165666B1

(12) United States Patent
Briggs et al.

(10) Patent No.: US 8,165,666 B1
(45) Date of Patent: Apr. 24, 2012

(54) SYSTEM AND METHOD FOR RECONSTRUCTING CARDIAC ACTIVATION INFORMATION

(75) Inventors: Carey Robert Briggs, La Jolla, CA (US); Sanjiv Narayan, La Jolla, CA (US)

(73) Assignees: Topera, Inc., Scottsdale, AZ (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/217,123

(22) Filed: Aug. 24, 2011

Related U.S. Application Data

(60) Provisional application No. 61/481,607, filed on May 2, 2011.

(51) Int. Cl.
*A61B 5/04* (2006.01)
(52) U.S. Cl. ...................................................... 600/515
(58) Field of Classification Search .......... 600/508–519; 607/4–5, 9, 25, 26
See application file for complete search history.

(56) References Cited

U.S. PATENT DOCUMENTS

| 5,366,487 | A | | 11/1994 | Adams et al. | |
|---|---|---|---|---|---|
| 5,439,483 | A | | 8/1995 | Duong-Van | |
| 5,450,846 | A | * | 9/1995 | Goldreyer | 600/374 |
| 5,480,422 | A | * | 1/1996 | Ben-Haim | 607/122 |
| 5,718,241 | A | * | 2/1998 | Ben-Haim et al. | 600/515 |
| 5,840,025 | A | * | 11/1998 | Ben-Haim | 600/424 |
| 5,868,680 | A | * | 2/1999 | Steiner et al. | 600/518 |
| 5,954,665 | A | * | 9/1999 | Ben-Haim | 600/515 |
| 6,066,094 | A | * | 5/2000 | Ben-Haim | 600/437 |
| 6,112,117 | A | | 8/2000 | KenKnight et al. | |
| 6,251,125 | B1 | | 6/2001 | KenKnight et al. | |
| 6,539,256 | B1 | | 3/2003 | KenKnight et al. | |
| 7,289,845 | B2 | | 10/2007 | Sweeney et al. | |
| 7,657,307 | B2 | | 2/2010 | Van Dam et al. | |
| 7,729,753 | B2 | | 6/2010 | Kremliovsky et al. | |
| 7,734,336 | B2 | | 6/2010 | Ghanem et al. | |
| 7,742,812 | B2 | | 6/2010 | Ghanem et al. | |
| 7,761,142 | B2 | | 7/2010 | Ghanem et al. | |

(Continued)

FOREIGN PATENT DOCUMENTS

CN 101461711 A 6/2009

(Continued)

OTHER PUBLICATIONS

Ciaccio, Edward J. et al., "Development of Gradient Descent Adaptive Algorithms to Remove Common Mode Artifact for Improvement of Cariovascular Signal Quality", Annals of Biomedical Engineering, vol. 35, No. 7, Jul. 2007, pp. 1146-1155.

(Continued)

*Primary Examiner* — Carl H Layno
*Assistant Examiner* — Roland Dinga
(74) *Attorney, Agent, or Firm* — Hoffmann & Baron, LLP

(57) ABSTRACT

An example system and method of reconstructing cardiac activation information are disclosed. A first cardiac signal and a second cardiac signal are processed via a computing device to determine whether there is a point of change in a derivative of the first cardiac signal with respect to a derivative of the second cardiac signal above a threshold. An activation onset time is assigned in the first cardiac signal at the point of change to define cardiac activation indicating a beat in the first cardiac signal if it is determined that the point of change is above the threshold.

20 Claims, 8 Drawing Sheets

U.S. PATENT DOCUMENTS

| | | |
|---|---|---|
| 7,761,150 B2 | 7/2010 | Ghanem et al. |
| 7,801,594 B1 | 9/2010 | Higham |
| 2006/0161206 A1 | 7/2006 | Efimov et al. |
| 2007/0239051 A1 | 10/2007 | Ghanem et al. |
| 2008/0269624 A1 | 10/2008 | Zhang et al. |
| 2009/0299424 A1 | 12/2009 | Narayan |
| 2010/0026543 A1 | 2/2010 | Tsai et al. |
| 2010/0094274 A1 | 4/2010 | Narayan et al. |
| 2010/0204592 A1* | 8/2010 | Hatib et al. .............. 600/485 |
| 2010/0324435 A1 | 12/2010 | Higham |
| 2011/0077540 A1 | 3/2011 | Belalcazar |
| 2011/0087121 A1* | 4/2011 | Zhang et al. ............. 600/515 |
| 2011/0112425 A1* | 5/2011 | Muhlsteff et al. ........ 600/534 |
| 2011/0251505 A1 | 10/2011 | Narayan et al. |

FOREIGN PATENT DOCUMENTS

| | | |
|---|---|---|
| EP | 2 269 691 A2 | 1/2011 |
| EP | 1 808 124 B1 | 4/2011 |
| WO | WO 2006/052838 A2 | 5/2006 |
| WO | WO 2007/078421 A2 | 7/2007 |
| WO | WO 2007/106829 A2 | 9/2007 |

OTHER PUBLICATIONS

Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.

Sun, Yan, et al., "Characteristic wave detection in ECG signal using morphological transform", BMC Cardiovascular Disorders, vol. 5, No. 28, 2005.

Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.

English-language translation of Chinese patent publication No. CN 101461711A, published Jun. 24, 2009.

U.S. Appl. No. 13/081,411, filed Apr. 6, 2011.

* cited by examiner

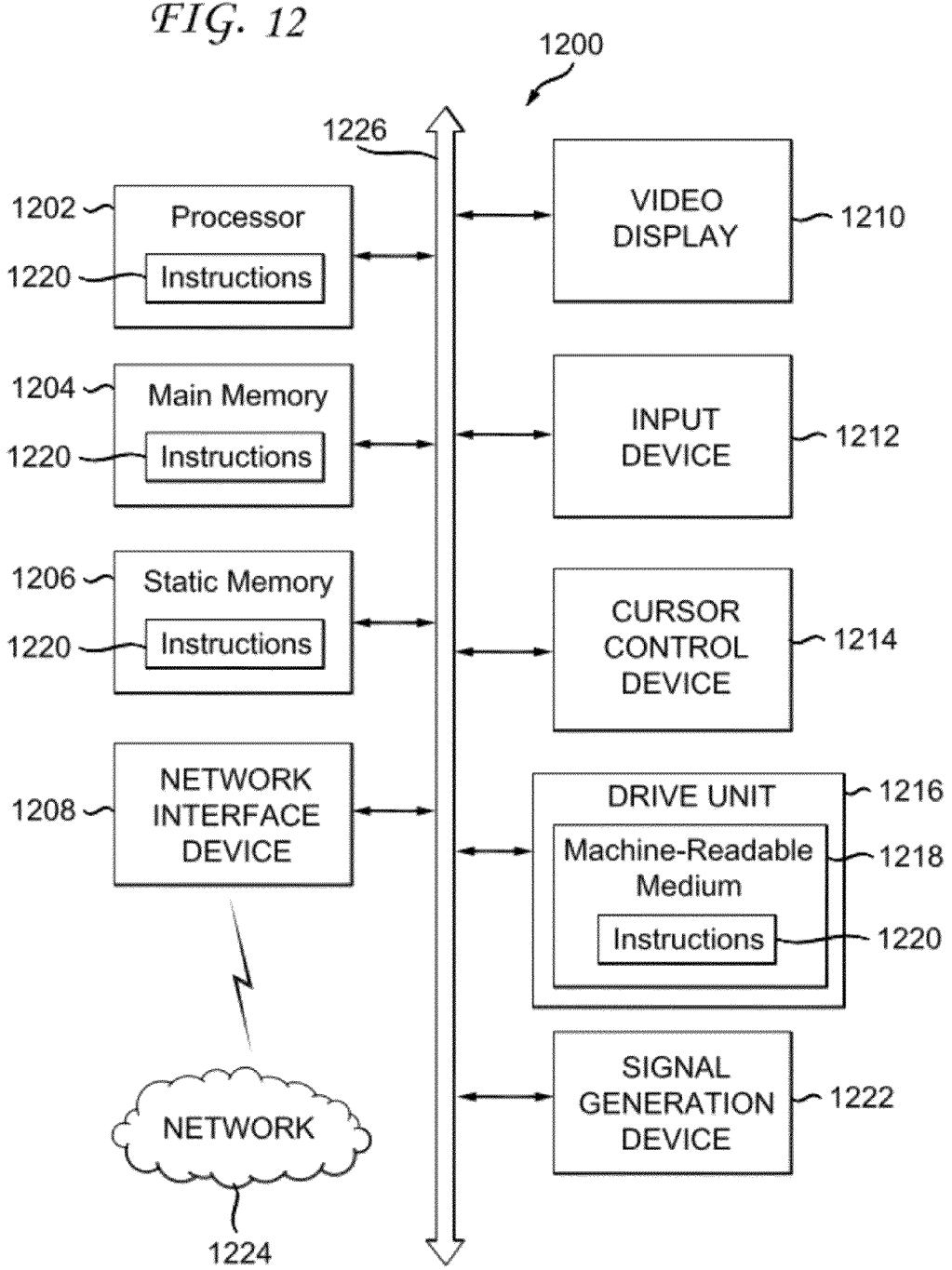

SYSTEM AND METHOD FOR RECONSTRUCTING CARDIAC ACTIVATION INFORMATION

CROSS REFERENCE TO RELATED APPLICATION

This application claims priority to and benefit of U.S. Provisional Patent Application No. 61/481,607 filed on May 2, 2011, which is incorporated herein by reference in its entirety.

FEDERAL GRANT

Some of the research described in this application was funded by Grants R01 HL83359, HL83359-S1 and HL103800 from the National Institutes of Health. The U.S. Government may therefore have certain rights in the invention.

BACKGROUND

1. Field

The present application relates generally to heart rhythm disorders. More specifically, the present application is directed to a system and method for reconstructing cardiac activation information (activation onset) associated with heart rhythm disorders.

2. Brief Discussion of Related Art

Heart (cardiac) rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), supraventricular ectopic complexes/beats (SVE) and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Treatment of heart rhythm disorders—particularly complex rhythm disorders of AF, VF and polymorphic VT—can be very difficult. Pharmacologic therapy for complex rhythm disorder is not optimal, with poor efficacy and significant side effects. Ablation has been used increasingly in connection with heart rhythm disorders by maneuvering a sensor/probe to the heart through the blood vessels, or directly at surgery, and delivering energy to a location of the heart that harbors a cause of the heart rhythm disorder to mitigate and in some cases to eliminate the heart rhythm disorder. However, in complex rhythm disorders ablation is often difficult and ineffectual because tools that identify and locate a cause of the heart rhythm disorder are poor and hinder attempts to deliver energy to the correct region of the heart to eliminate the disorder.

Certain systems and methods are known for treating simple heart rhythm disorders. In a simple heart rhythm disorder (e.g., atrial tachycardia), consistent activation onset patterns from beat to beat can generally be traced back to an earliest location, which can be ablated to mitigate and in some cases to eliminate the disorder. Even in simple heart rhythm disorders, such ablation of the cause of a heart rhythm disorder is challenging and experienced practitioners often require hours to ablate simple rhythm disorders with consistent beat-to-beat activation patterns, such as atrial tachycardia.

There are no known systems and methods that have been successful with respect to identifying causes for the complex rhythm disorders such as AF, VF or polymorphic VT. In a complex rhythm disorder, an earliest location of activation onsets cannot be identified because activation onset patterns change from beat to beat, and are "continuous" such that there is no identifiable earliest point (or start) or latest point (or end).

Diagnosing and treating heart rhythm disorders often involves the introduction of a catheter having a plurality of sensors/probes into the heart through the blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat in timing and often in shape and number of its deflections, enabling identification of activation onsets at each sensor location. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are at or near the sensor location in the heart (i.e., local activation) versus a further removed location still sensed by the sensor in the heart (i.e., far-field activation) or simply noise from another part of the patient's heart, other anatomic structures, movement or motion of the sensor relative to the heart or external electronic systems.

There are no known systems and methods that have been able to reconstruct cardiac activation information (onsets) in variously shaped signals associated with heart rhythm disorders, especially in complex rhythm disorders, to facilitate identification of a cause of the heart rhythm disorders and their elimination.

SUMMARY

The present invention is applicable to reconstructing activation information of various rhythm disorders, including heart rhythm disorders, as well as other biological rhythm disorders, such as neurological seizures, esophageal spasms, bladder instability, irritable bowel syndrome, and other biological disorders for which biological activation information can be reconstructed to permit determination, diagnosis, and/or treatment of the cause or source of the disorders. It is particularly useful, however, in complex rhythm disorders which result in complex activation patterns, and especially useful in complex rhythm disorders of the heart, in order to find the cause(s) or source(s) of the disorders such that they can be treated with expediency.

Complex heart rhythm disorders typically result in activation patterns that are extremely difficult to decipher and the ability to determine accurate activation information of heart beats in complex disorders has previously not been possible. Among the advantages of the present invention is the ability to reconstruct cardiac activation information such that a determination of the cause and/or source of the disorder can be determined and treated. Another advantage is that the present invention provides a system and method which can be carried out rapidly while a sensing device—such as a catheter having sensors thereon—is used in or near the patient and can be followed by treatment of cardiac tissue to ameliorate the disorder and in many cases cure the disorder. Treatment may thus occur immediately upon computing the reconstructed cardiac information, since it will provide the location(s) of the cause or source of the disorder.

Prior systems and methods suffered from the inability to determine the source of heart rhythm disorders and consequently provided no means of targeting the source for meaningful and curative treatment. Additionally, prior systems and methods required numerous and complex steps of treatment and yet still failed to provide a means of reconstructing cardiac activation information sufficient to identify the cause(s) or source(s) of the heart rhythm disorder.

In contrast to prior systems and methods, the present invention provides a relatively few number of steps to reconstruct the activation information in order to determine the activation onset times at various sensor locations for a heart beat amidst the virtually indiscernible activation patterns.

As used herein, reconstruction is a process of identifying activation onset time in a cardiac or biological signal at a sensor location distinct from nearby or adjacent sensor locations for one or more beats of a biological or cardiac rhythm disorder.

As used herein, activation onset time is a time point at which activation commences in a cell or tissue, as opposed to other time points during activation.

As used herein, activation is a process whereby a cell commences its operation from a quiescent (diastolic) state to an active (electrical) state.

In accordance with an embodiment or aspect, a system to reconstruct cardiac activation information is disclosed. The system includes at least one computing device. The computing device is configured to process a first cardiac signal and a second cardiac signal to determine whether there is a point of change in a derivative of the first cardiac signal with respect to a derivative of the second cardiac signal above a threshold. The computing device is further configured to assign an activation onset time in the first cardiac signal at the point of change to define cardiac activation indicating a beat in the first cardiac signal if it is determined that the point of change is above the threshold. The point of change can be determined at about the same time point for both the first cardiac signal and the second cardiac signal.

The computing device can form a composite cardiac signal from the first cardiac signal and the second cardiac signal, and can determine ratio values at a plurality of points in the first cardiac signal. Each ratio value can represent a difference between the derivative of the second cardiac signal and a derivative of the composite cardiac signal to a difference between the derivative of the first cardiac signal and the derivative of the composite cardiac signal. The computing device can also select as the point of change in the first cardiac signal a point having a largest ratio value from the determined ratio values.

The computing device can match at least one characteristic of the first cardiac signal to at least one characteristic of a reference cardiac signal in a catalog of cardiac signals if it is determined that there is no point of change above the threshold. Thereafter, the computing device can assign an activation onset time in the first cardiac signal as an onset time of the reference cardiac signal to define cardiac activation indicating a beat in the first cardiac signal.

The computing device can iteratively select pairs of cardiac signals from a plurality of cardiac signals. Each pair can include a first cardiac signal and different second cardiac signal. The computing device can perform processing and assignment for each of the pairs to define multiple cardiac activations indicating beats for the first cardiac signal in each of the pairs. The computing device can further reconstruct a cardiac activation pattern based on assigned activation onset times of cardiac activations from the plurality of cardiac signals to indicate a source of a cardiac rhythm disorder. The computing device can also display the reconstructed cardiac activation pattern to facilitate treatment of cardiac tissue at the source to suppress, lessen or eliminate the cardiac rhythm disorder.

In accordance with another embodiment or aspect, a method of reconstructing cardiac activation information is disclosed. The method includes processing a first cardiac signal and a second cardiac signal via a computing device to determine whether there is a point of change in a derivative of the first cardiac signal with respect to a derivative of the second cardiac signal above a threshold. The method further includes assigning an activation onset time in the first cardiac signal at the point of change to define cardiac activation indicating a beat in the first cardiac signal if it is determined that the point of change is above the threshold. The point of change can be determined at about the same time point for the first cardiac signal and the second cardiac signal.

The determination of the point of change in the method can include the following operations. A composite cardiac signal can be formed from the first cardiac signal and the second cardiac signal. Ratio values at a plurality of points in the first cardiac signal can be determined. Each ratio value can represent a difference between the derivative of the second cardiac signal and a derivative of the composite cardiac signal to a difference between derivative of the first cardiac signal and the derivative of the composite cardiac signal. A point having a largest ratio value from the determined ratio values can be selected as the point of change in the first cardiac signal.

If it is determined that there is no point of change above the threshold, the method can include matching at least one characteristic of the first cardiac signal to at least one characteristic of a reference cardiac signal in a catalog of cardiac signals. Thereafter, an activation onset time of the reference cardiac signal can then be assigned as an activation onset time in the first cardiac signal to define cardiac activation indicating a beat in the first cardiac signal.

The method for reconstructing cardiac activation information can further include iteratively selecting pairs of cardiac signals from a plurality of cardiac signals. Each pair includes a first cardiac signal and different second cardiac signal. The operations of processing and assigning for each of the pairs can be performed to define multiple cardiac activations indicating beats for the first cardiac signal in each of the pairs. Thereafter, a cardiac activation pattern can be reconstructed based on assigned activation onset times of cardiac activations from the plurality of cardiac signals to indicate a source of a cardiac rhythm disorder.

In accordance with a further embodiment aspect, a method of treating a cardiac rhythm disorder is disclosed. The method includes iteratively accessing a first cardiac signal and a second cardiac signal from a plurality of cardiac signals. The first cardiac signal and the second cardiac signal are processed via a computing device to determine whether there are points of change in a derivative of the first cardiac signal with respect to a derivative of the second cardiac signal above a threshold. Activation onset times are assigned to the first cardiac signal at the points of change to define cardiac activations indicating beats in the first cardiac signal if it is determined that the points of change are above the threshold. The method further includes reconstructing a cardiac activation pattern based on the assigned activation onset times to indicate a source of the rhythm disorder. Still further, the method includes treating cardiac tissue at the source to suppress or eliminate the rhythm disorder.

These and other purposes, goals and advantages of the present application will become apparent from the following detailed description read in connection with the accompanying drawings.

BRIEF DESCRIPTION OF THE DRAWINGS

Some embodiments or aspects are illustrated by way of example and not limitation in the figures of the accompanying drawings in which:

FIG. 12 is a block diagram of an illustrative embodiment of a general computer system.

DETAILED DESCRIPTION

A system and method for reconstructing cardiac activation information associated with heart rhythm disorders are disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

Figure 1:
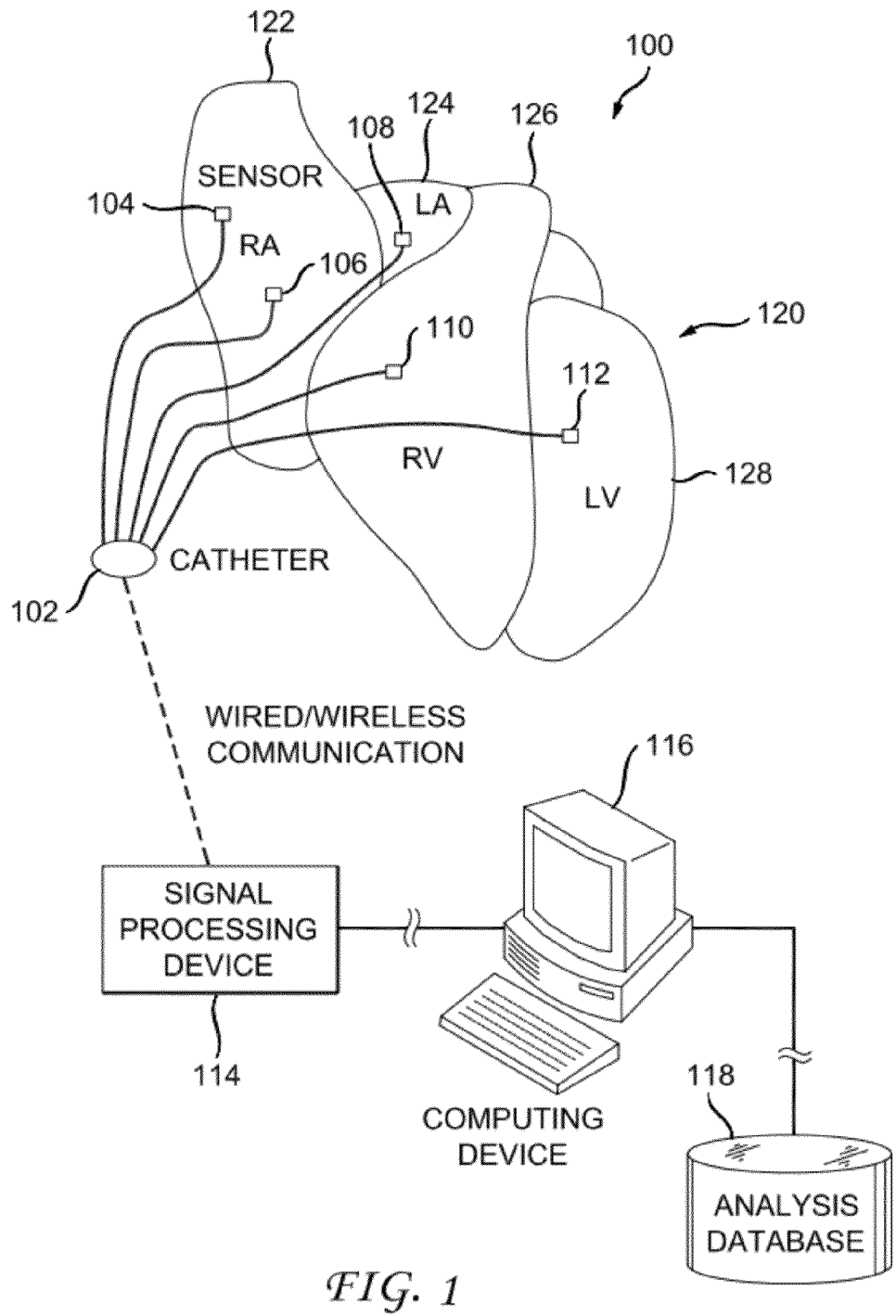
FIG. 1 illustrates an example cardiac activation reconstruction system.

FIG. 1 illustrates an example cardiac activation reconstruction system 100. The example system 100 is configured to detect and reconstruct cardiac activation information collected/detected from a patient's heart in connection with a heart rhythm disorder. The heart includes a right atrium 122, left atrium 124, right ventricle 126 and left ventricle 128.

The example system 100 includes a catheter 102, signal processing device 114, computing device 116 and analysis database 118.

The catheter 102 is configured to detect cardiac activation information in the heart and to transmit the detected cardiac activation information to the signal processing device 114, either via a wireless or wired connection. The catheter includes a plurality of probes/sensors 104-112, which can be inserted into the heart through the patient's blood vessels.

In some embodiments or aspects, one or more of the sensors 104-112 are not inserted into the patient's heart. For example, some sensors may detect cardiac activation via the patient's surface (e.g., electrocardiogram) or remotely without contact with the patient (e.g., magnetocardiogram). As another example, some sensors may also derive cardiac activation information from cardiac motion of a non-electrical sensing device (e.g., echocardiogram). In various embodiments or aspects, these sensors can be used separately or in different combinations, and further these separate or different combinations can also be used in combination with sensors inserted into the patient's heart.

The sensors 104-112, which are positioned at sensor locations in the heart under consideration, can detect cardiac activation information at the sensor locations and can further deliver energy to ablate the heart at the sensor locations. It is noted that the sensors 104-112 can also detect cardiac activation information from overlapping regions of the heart (e.g., right atrium 122 and left atrium 124).

The signal processing device 114 is configured to process (e.g., clarify and amplify) the cardiac activation information detected by the sensors 104-112 at the sensor locations into electrogram signals and to provide the processed cardiac signals to the computing device 116 for analysis or processing in accordance with methods disclosed herein. In processing the cardiac activation information from the sensors 104-112, the signal processing device 114 can subtract cardiac activation information from overlapping regions of the heart 120 to provide processed cardiac signals to the computing device 116 for analysis. While in some embodiments or aspects, the signal processing device 114 is configured to provide unipolar signals, in other embodiments or aspects, the signal processing device 114 can provide bipolar signals.

The computing device 116 is configured to receive (or cccess) cardiac signals from the signal processing device 114 and further configured to analyze or process the cardiac signals in accordance with methods, functions or logic disclosed herein to reconstruct cardiac activation information in the cardiac signals such that it is possible to locate a cause of the heart rhythm disorder and to eliminate the cause.

For example, the computing device 116 can process a first cardiac signal and a second cardiac signal from the received cardiac signals to determine whether there is a point of change in a derivative of the first cardiac signal with respect to a derivative of the second cardiac signal above a threshold. The computing device 116 can then assign an activation onset time in the first signal at the point of change to define cardiac activation indicating a beat in the first signal if it is determined that the point of change is above the threshold.

As another example, the computing device 116 can iteratively select pairs of cardiac signals from the received cardiac signals, each pair having a first cardiac signal and second cardiac signal. The computing device 116 can process and assign for each of the pairs in order to define multiple cardiac activations indicating beats for the first cardiac signal in each of the pairs. For example, the computing device 116 is configured to perform processing and assigning to define multiple cardiac activations indicating beats in the first cardiac signal. The computing device 116 can then reconstruct a cardiac activation pattern based on assigned activation onset times of cardiac activations from the received cardiac signals to indicate a source of a rhythm disorder. In some embodiments or aspects, the computing device 116 can also display the reconstructed cardiac activation pattern to facilitate treatment of cardiac tissue at the source to suppress, lessen or eliminate the cardiac rhythm disorder.

The analysis database 118 is configured to support or aid in the analysis of the signals by the computing device 116. In some embodiments or aspects, the analysis database 118 can store a catalog of reference signals and associated activations to enable the computing device 116 to determine an activation onset associated with a signal being considered (e.g., when point of change is below threshold during a time window), as will be described in greater detail herein.

Figure 2:
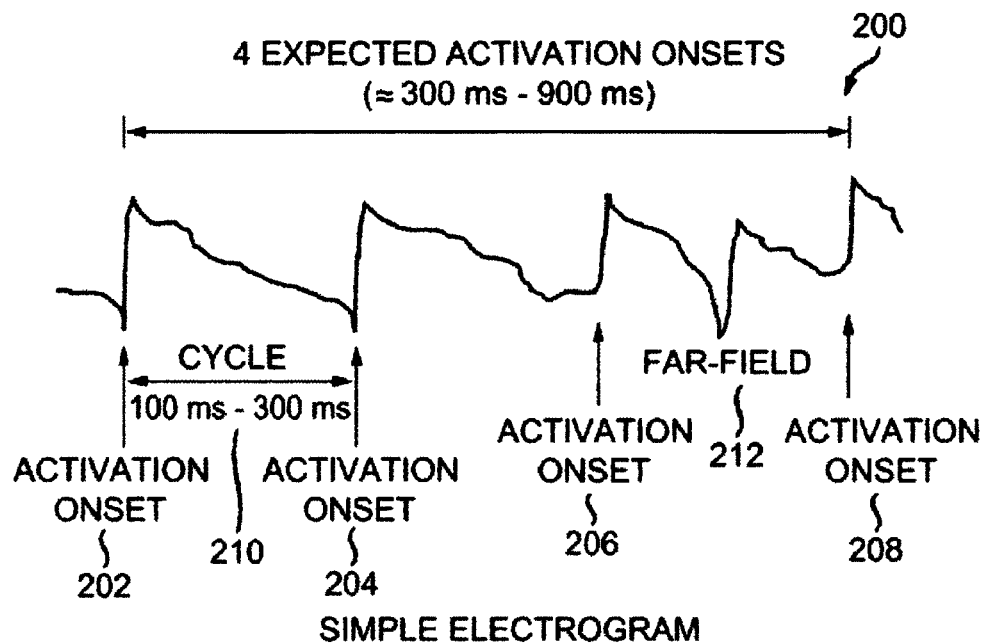
FIG. 2 illustrates an example simple electrogram signal of a heart rhythm disorder from a sensor positioned at a sensor location in a heart illustrated in FIG. 1.

FIG. 2 illustrates an example simple electrogram signal 200 of a heart rhythm disorder from a sensor positioned at a sensor location in the heart 120. For example, sensor 104 of catheter 102 can be positioned at a sensor location in the right atrium 122, as shown in FIG. 1. As an example, the heart rhythm disorder can be a complex rhythm disorder AF, VF and polymorphic VT, or another heart rhythm disorder.

The example signal 200 is for a time period between about 300 ms and about 900 ms. During this time period, the signal 200 is expected to have four (4) local activation onsets 204-208, e.g., those activation onsets that originate at or near (locally to) the sensor location in the heart 120 of sensor 104. Specifically, based on established observations in heart rhythm disorders, cycle length between activation onsets of about 100 ms to about 300 ms can be expected for AF, and cycle length between activation onsets of about 180 ms to about 240 ms can be expected for complex ventricular arrhythmias. As an example, cycle length 210 of about 100 ms to about 300 is expected between activation onset 202 and activation onset 204. In the example signal 200, the activation onsets 204-208 are generally identifiable as having a small degree of baseline wander superposed in the local signal with few far-field artifacts that could be mistaken as local activity. Local activity in this example can be characterized by an activation onset with a sharp inflection point and high slope, followed by a period of gentle, low-deviation slope representing repolarization, typically lasting between about 100 ms and 250 ms.

In the example signal 200, an example far-field deflection 212 is illustrated between location activation onset 206 and local activation onset 208, e.g., an activation onset that originates at a location in the heart 120 that is different than the sensor location associated with the sensor 104. Specifically, the heart 120 at the sensor location associated with sensor 104 cannot physiologically activate again after activation onset 206 in a shorter cycle than about 100 ms to about 300 ms because local tissue must undergo repolarization. Moreover, the deflection 212 cannot be local to the sensor location associated with the sensor 104 when the deflection 212 is also significantly present in signals collected by neighbor sensors in multiple directions to sensor 104. For example, the far-field deflection 212 detected by sensor 104 can be associated with activation onset at a sensor location associated with sensor 106.

Figure 3:
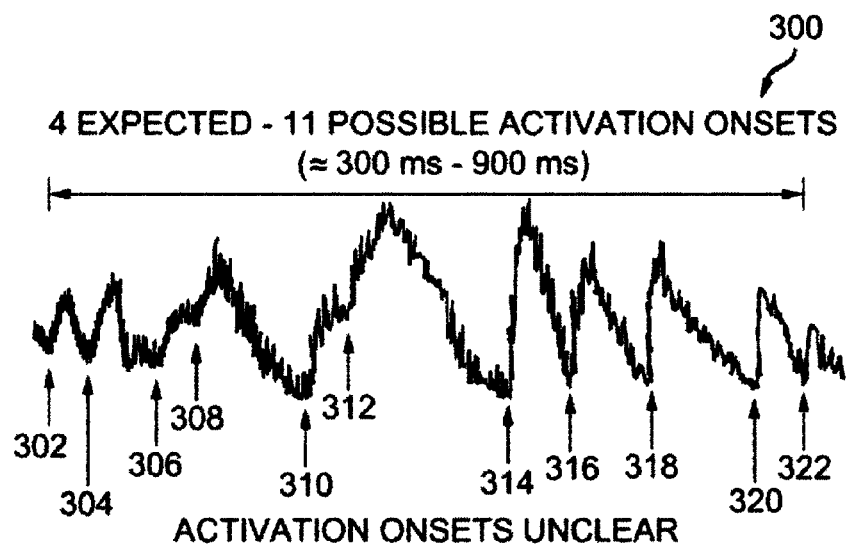
FIG. 3 illustrates an example complex electrogram signal of a heart rhythm disorder from a sensor positioned at a sensor location in a heart illustrated in FIG. 1.

FIG. 3 illustrates an example complex electrogram signal 300 of a heart rhythm disorder from a sensor positioned at a sensor location in the heart 120. For example, sensor 106 of catheter 102 can be positioned at a sensor location in the right atrium 122, as shown in FIG. 1. As an example, the heart rhythm disorder can be a complex rhythm disorder AF, VF and polymorphic VT, or another heart rhythm disorder.

Similarly to example signal 200, example signal 300 is for a time period between about 300 ms and about 900 ms. During this time period, the signal 300 is expected to have four (4) local activation onsets, e.g., activation onsets that originate locally to the sensor location in the heart 120 of sensor 106. However, in the example signal 300 there are eleven (11) possible activation onsets 302-322. Multiple deflections of short duration (shorter than shortest cycle length of about 100 ms) caused by the heart rhythm disorder makes the discernment of local activation onsets at the sensor location of sensor 104 as opposed to far-field activations or simply noise prohibitively difficult.

Figure 4:
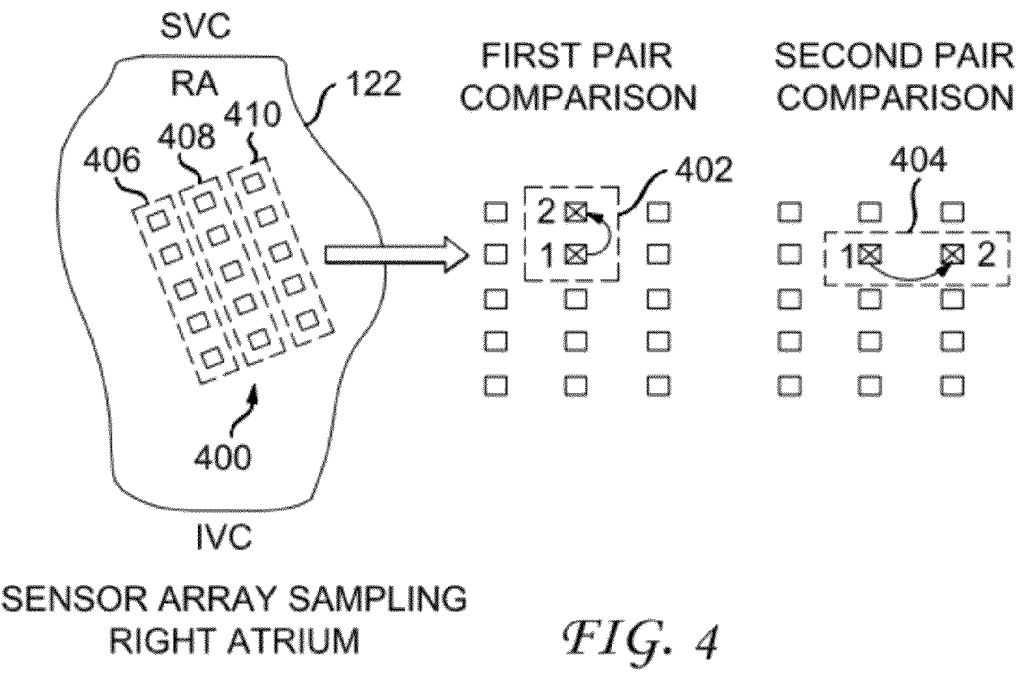
FIG. 4 illustrates an example array of sensors of a catheter illustrated in FIG. 1 and an example selection of signals from the sensors to reconstruct cardiac activation information.

FIG. 4 illustrates an example array of sensors 400 of catheter 102 and an example selection of signals from the sensors to reconstruct cardiac activation information (e.g., activation onsets). The array 400 includes fifteen (15) example sensors for simplicity and clarity of the description. It is to be understood that the array 400 can include fewer or more sensors to as may be determined to cover different portions of the heart 120. In some embodiments or aspects, the array 400 can include 160 or more sensors.

The sensors of the array 400 are shown in example spatial arrangement with respect to the right atrium 122 of the heart 120. Similarly, the array 400 can be spatially arranged in other chambers of the heart, e.g., left atrium, right ventricle, left ventricle, or for combinations of chambers including the endocardial or epicardial surfaces. In FIG. 4, the spatial arrangement of electrodes in the array 400 is shown to be uniform and planar for simplicity and clarity of the description. However, the heart 120 is not a uniform or planar structure. Accordingly, the spatial arrangement of electrodes in the array 400 can be varied with respect to the shape of the heart 120 to improve detection of electric activity in the heart 120.

In one example embodiment or aspect, catheter 102 of FIG. 1 can be a basket catheter with the example sensors of the array 400 disposed in spatial arrangements along splines 406-408 of the basket catheter 102. Different catheters with various spatial arrangements of the sensors in the sensor array 400 can be used, such as spiral, radial spokes or other spatial arrangements.

Pairs of sensors (signals of sensors) in the array 400 are iteratively selected for processing as will be described in greater detail herein in order to reconstruct cardiac activation information (activation onsets) of the heart 120 in the right atrium 122, or another chamber in which the array 400 may be disposed.

As illustrated at 402, an analysis signal (1) is selected for processing. A reference signal (2)—a neighbor to the analysis signal (1)—is then selected to form a first pair that is processed to determine activation onsets in the analysis signal (1). Similarly, as illustrated at 404, an analysis signal (1) is selected for processing. A reference signal (2)—another neighbor to the analysis signal (1)—is then selected to form a second pair that is processed to determine activation onsets in the analysis signal (1). The activation onsets from the first pair and the second pair of signals can be stored in memory of computing device 116 or database 118 of FIG. 1. The neighboring sensors (signals) can but do not have to be adjacent, as will be described in greater detail below.

The selections and processing are repeated for the sensors of the array 400 (signals) that neighbor the analysis signal (1). The activation onsets in the analysis signal (1) for all pairs of signals can also be stored in memory of computing device 116 or database 118. Thereafter, another analysis signal is selected and the selections and processing are repeated for that analysis signal. In this fashion, each of the plurality of analysis signals in array 400 is processed against its neighboring signals. The number of neighboring signals for a given analysis signal can be fewer or greater depending on the spatial arrangement of the sensors in the array 400, the chamber of the heart analyzed and the heart rhythm disorder treated.

Figure 5:
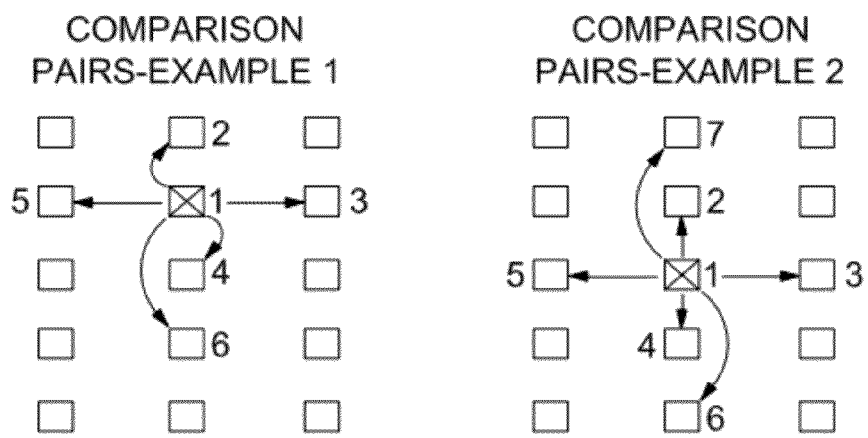
FIG. 5 illustrates example comparison pairs of signals from the sensors of the array illustrated in FIG. 4.

FIG. 5 illustrates example comparison pairs of signals from the sensors of the array 400 illustrated in FIG. 4. Neighbor signals can include not only those signals that are immediately adjacent to the analysis signal but also those signals not adjacent to the analysis signal. Spatially separating the paired sensors can have the effect of spatially extending the area over which deflections are considered to be local activity. Local activity is therefore approximately defined by the separation of the paired sensors. As illustrated in example 1 of FIG. 5, selected analysis signal (1) is processed against adjacent signals (2)-(5) and also against a non-adjacent signal (6). As further illustrated in example 2 of FIG. 5, selected analysis signal (1) is processed against adjacent signals (2)-(5) and also against a non-adjacent signals (6) and (7). While closest neighbor signals are preferred, neighbor signals in various spatial orientations with respect to the analysis signal can be used.

For each analysis signal, there could be a plurality of reference signals (e.g., four (4) reference signals or greater). A final activation onset in the analysis signal is determined with reference to or based on the combination of the reference signals' possible activation onsets. Specifically, the activation onsets determined from each pair can be referenced against each other to check for correspondence or association of activations in the analysis signal. An activation onset for the analysis signal is finalized based on the possible activation onsets of the referenced pairs of signals.

The final activation onset for the analysis signal can be determined in various ways. In one embodiment or aspect, the final activation onset for the analysis signal can be determined based on an average of the possible activation onsets from the various pairs of referenced signals. In another embodiment or aspect, the final activation onset for the analysis signal can be determined based on an average of the possible activation onsets from those pairs of signals in which a majority of the possible activation onsets are within a predetermined time interval of each other (e.g., ±5 ms). The time interval used can be chosen to be lower or higher. Alternatively, the final activation can also be determined by performing a "center-of-mass" calculation weighted by the significance value of each of the possible activation onsets in the majority, or by analysis of a predominant direction of activation onsets relative to sensor locations.

With reference to example 1 in FIG. 5, if an analysis signal has been determined to have possible activation onsets of 170 ms, 190 ms, 193 ms, 165 ms and 172 ms in connection with the five (5) reference signal pairs, respectively, then the final activation onset for the analysis signal can be determined to be (170+165+172)/3=169 ms. The activation onsets of 190 ms and 193 ms that are outside the time interval can be discounted from the determination of the final activation onset for the analysis signal. The final activation onset determined for each signal can be saved in the database 118 of FIG. 1.

While in the forgoing examples for the sake of brevity and clarity, only one activation onset was determined for the analysis signal in connection with each reference signal, it should understood that each signal (from a sensor of array 400) can represent multiple successive analysis intervals (e.g., activation cycles) as illustrated in FIG. 2, each of which can have an activation onset as determined based on the same time interval of multiple reference signals (neighboring sensors of array 400).

Figure 6:
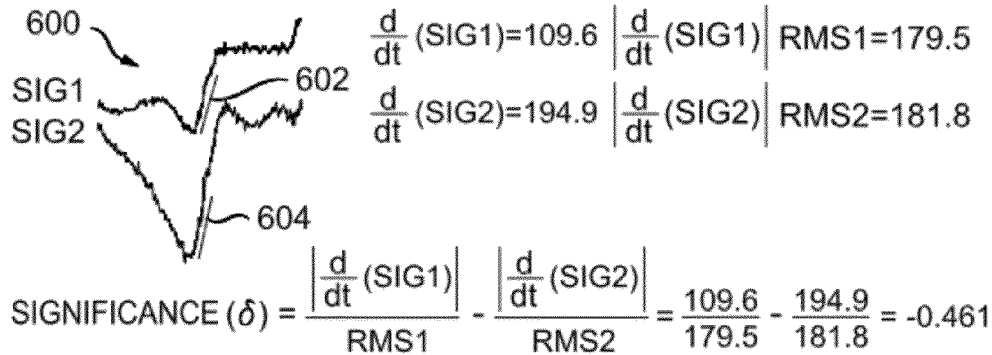
FIG. 6 is an illustration of an example signal pair comparison of analysis signal (SIG1) and reference signal (SIG2)

FIG. 6 is an illustration of an example signal pair comparison 600 of example analysis signal (SIG1) and example reference signal (SIG2). For example, the signals can be from comparison pair 402 (or comparison pair 404) illustrated in FIG. 4, or from any comparison pair illustrated in FIG. 5. It is noted that the signals are illustrative and occur during the same analysis interval. As noted herein, the signals can have multiple successive analysis intervals (e.g., activation cycles), as illustrated in FIG. 2.

The signals are processed at one or more successive time points (e.g., every millisecond, two milliseconds, or other time points) to determine whether there is a point of change in a derivative of the analysis signal with respect to a derivative of the reference signal above a threshold. The point of change can be determined from one or more of slope, amplitude, timing and shape for the first cardiac signal and the second cardiac signal. It is noted that in some embodiments or aspects, processing of some time points can be omitted (e.g., every other time point or two of three time points). A first derivative (or second derivative can be used) is determined for each of the time points in the signals. A root mean squared is determined for each of the signals. For example, RMS1 and RMS2 are determined by taking a root mean squared of the derivatives for the entire signal of each of the signals (e.g., all activation cycles). RMS can be used to normalize the amplitude of the signals with respect to one another, such that amplitudes (e.g., voltage) of the deflections in the signals do not affect the processing of the signals as described below.

A time point (same time point or about the same time point) is successively selected from each of the signals (SIG1, SIG2) for consideration and processing. For each time point under consideration, a time increment 602, 604 in each signal starting at that time point can be considered. For example, a time increment of 10 ms can be used. Different time increments can be selected. A line which is pinned to the point under consideration in each signal and which provides the best fit to the time points in the time increment of each signal is determined. The determined lines represent the slopes (e.g., volts/per second) of the signals for the selected time point. More specifically, the determined lines represent slopes of the signals at the selected time point for the same time increment (e.g., 10 ms). A significance value ($\delta$) is determined with respect to the slopes.

The significance value can be determined by taking an absolute value of the first slope over its associated root mean squared value and subtracting an absolute value of the second slope over its associated root mean squared value. A determination is made as to whether the resulting ($\delta$)=−0.461 is above a significance threshold (e.g., 0.25). The significance threshold indicates that there is a potentially significant point of change (based on slopes) for the time point in the signals under consideration, e.g., that the derivatives diverge sufficiently from each other. In the example signal pair comparison 600, the significance value ($\delta$)=−0.461 is below the significance threshold of 0.25. The low significance value indicates that the deflection in SIG1 is far-field and not sufficiently local to a sensor location from which the signal originated, e.g., a sensor shown in FIG. 4. Accordingly, there is no potentially significant point of change in the example signal pair comparison 600.

As noted herein, the signals can have multiple successive analysis intervals (e.g., activation cycles), as illustrated in FIG. 2. In each analysis interval, it is possible to have zero, one or more potentially significant points of change as described above. The time point under consideration and the potentially significant point(s) of change can be recorded, such as in database 118.

Figure 7:
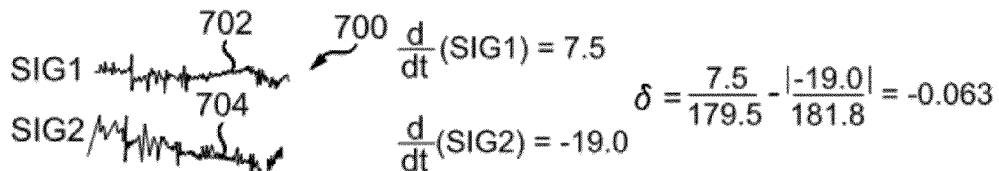
FIG. 7 is an illustration of another example signal pair comparison of analysis signal (SIG1) and reference signal (SIG2)

FIG. 7 is an illustration of an example signal pair comparison 700 of example analysis signal (SIG1) and example reference signal (SIG2). Similarly, the signals can be from comparison pair 402 (or comparison pair 404) illustrated in FIG.

4, or from any comparison pair illustrated in FIG. 5. The signals are illustrative and occur during the same analysis interval. As noted herein, the signals can have multiple successive analysis intervals (e.g., activation cycles), as illustrated in FIG. 2.

The signals are processed at one or more successive time points to determine whether there is a point of change in a derivative of the analysis signal with respect to a derivative of the reference signal above a threshold. In some embodiments or aspects, processing of some time points can be omitted (e.g., every other time point or two of three time points). A first derivative (or second derivative) is determined for each of the time points in the signals. A root mean squared is further determined for each of the signals. A time point (same time point or about the same time point) is successively selected from each of the signals (SIG1, SIG2) for consideration and processing. For each time point under consideration, a time increment 702, 704 (e.g., 10 ms) in each signal starting at that time point can be considered. A line which is pinned to the point under consideration in each signal and which provides the best fit to the time points in the time increment of each signal is determined. The determined lines represent the slopes (e.g., volts/per second) of the signals for the selected time point. More specifically, the determined lines represent the slopes at the selected time point for the same time increment. A significance value ($\delta$) is determined with respect to the slopes.

The significance value can be determined by taking an absolute value of the first slope over its associated root mean squared value and subtracting an absolute value of the second slope over its associated root mean squared value. A determination is made as to whether the resulting ($\delta$)=−0.063 is above a significance threshold (e.g., 0.25). In the example signal pair comparison 700, the significance value ($\delta$)=−0.063 is well below the significance threshold of 0.25. The low significance value indicates low amplitude noise. Accordingly, there is no potentially significant point of change in the example signal pair comparison 700.

A noise level can be defined as fraction of the significance threshold or can be defined programmatically in various ways. For example, noise level can be one-tenth (0.025) of the significance threshold (0.25). A different fraction level can be selected. As another example, the noise level can be defined as a Gaussian standard deviation of a plurality of significance values. Other ways of defining the noise level are contemplated. It is noted that the significance threshold (e.g., 0.25) is higher than the noise level that can be associated with the analysis signal and reference signal in the example signal pair comparison 700. Accordingly, a point of change at or below noise level can be associated with one or more signals from other regions of a heart, respiratory system, gastrointestinal tract, neurological system as well as electronic interference.

As noted herein, the signals can have multiple successive analysis intervals (e.g., activation cycles) and in each analysis interval, it is possible to have zero, one or more potentially significant points of change as described above. The time point under consideration and the potentially significant point(s) of change can be recorded, such as in database 118.

Figure 8:
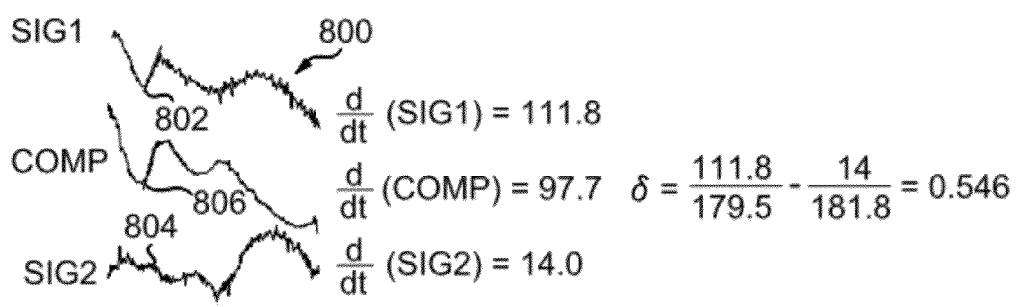
FIG. 8 is an illustration of a further example signal pair comparison of analysis signal (SIG1) and reference signal (SIG2) utilizing a composite signal.

FIG. 8 is an illustration of an example signal pair comparison 800 of example analysis signal (SIG1) and example reference signal (SIG2) utilizing a composite signal. As in the other examples, the signals can be from comparison pair 402 (or comparison pair 404) illustrated in FIG. 4, or from any comparison pair illustrated in FIG. 5. The signals are illustrative and occur during the same analysis interval. As noted herein, the signals can have multiple successive analysis intervals (e.g., activation cycles), as illustrated in FIG. 2.

The signals are processed at one or more successive time points to determine whether there is a point of change in a derivative of the analysis signal with respect to a derivative of the reference signal above a threshold. In some embodiments or aspects, processing of some time points can be omitted (e.g., every other time point or two of three time points). A first derivative (zero order derivative or second derivative) is determined for each of the time points in the signals. A root mean squared is further determined for each of the signals. A time point (same time point or about the same time point) is successively selected from each of the signals (SIG1, SIG2) for consideration and processing. For each time point under consideration, a time increment 802, 804 (e.g., 10 ms) in each signal starting at that time point can be used. A line which is pinned to the point under consideration in each signal and which provides the best fit to the time points in the time increment of each signal is determined. The determined lines represent the slopes (e.g., volts/per second) of the signals for the selected time point. More specifically, the determined lines represent the slopes of the signals at the selected time point for same time increment. A significance value ($\delta$) is determined with respect to the slopes.

In some embodiments or aspects, the significance value can be determined by taking an absolute value of the first slope over its associated root mean squared value and subtracting an absolute value of the second slope over its associated root mean squared value. A determination is made as to whether the resulting ($\delta$)=0.546 is above a significance threshold (e.g., 0.25). In the example signal pair comparison 800, the significance value ($\delta$)=0.546 is determined to be above the significance threshold of 0.25.

Accordingly, there is a potentially significant point of change in the example signal pair comparison 800 at the time point under consideration. As noted herein, the signals can have multiple successive analysis intervals (e.g., activation cycles) and in each analysis interval, it is possible to have zero, one or more potentially significant points of change as described above. The time point under consideration and the potentially significant point(s) of change can be recorded, such as in database 118.

In other embodiments or aspects, the significance value can be determined with respect to a composite signal. Specifically, a composite signal (COMP) is computed by subtracting SIG2 (reference signal) from SIG1 (analysis signal), e.g., COMP=SIG2−SIG1. The composite signal can represent a bipolar signal (COMP) of constituent unipolar signals (SIG1, SIG2). In alternate embodiments or aspects, the composite signal COMP can also be computed by adding signals SIG1 and SIG2. The signals in the signal pair comparison 800 are illustrative and occur during the same analysis interval. As noted herein, the signals can have multiple successive analysis intervals (e.g., activation cycles), as illustrated in FIG. 2.

The signals SIG1, SIG2 are processed at one or more successive time points with respect to the composite signal COMP to determine whether there is a point of change in a derivative of the analysis signal with respect to a derivative of the reference signal above a threshold. A first derivative (or second derivative) is determined for each of the time points in the signals, SIG1, SIG2, COMP. A time point (same time point or about the same time point) is successively selected from each of the signals (SIG1, SIG2, COMP) for consideration and processing. For each time point under consideration, a time increment 802, 804, 806 (e.g., 10 ms) in each signal starting at that time point can be considered. A line which is pinned to the point under consideration in each signal and which provides the best fit to the time points in the time increment of each signal is determined. The determined lines represent the slopes (e.g., volts/per second) of the signals for the selected time point. More specifically, the determined lines represent the slopes of the signals at the selected time point for the same time increment. A significance value (δ) is determined with respect to the slopes.

In the embodiments or aspects employing the composite signal, the significance value (δ) can be determined by a ratio taking an absolute value of the second slope and subtracting an absolute value of the composite slope, and dividing by a logarithm of a result of an absolute value the first slope subtracting an absolute value of the composite slope. The resulting significance value for the time point under consideration is (δ)=31.63. Significance values can be computed for all points under consideration. A significance threshold can be determined to be an average of the computed significance values (δ) plus a standard deviation. Thereafter, only those significance values (δ) that are above the significance threshold can be considered to be potentially significant points of change for the comparison pair 800. For the example signals in the signal pair comparison 800 of FIG. 8, the determined significance threshold can be 10. It is noted that the significance value(s) that is above the significance threshold generally extends substantially above the significance threshold. For example, a significance value (δ)—having the largest ratio—can therefore be selected.

Accordingly, there is a potentially significant point of change in the example signal pair comparison 800 at the time point under consideration. As noted herein, the signals can have multiple successive analysis intervals (e.g., activation cycles) and in each analysis interval, it is possible to have zero, one or more potentially significant points of change as described above. The time point under consideration and the potentially significant point(s) of change can be recorded, such as in database 118.

Figure 9:
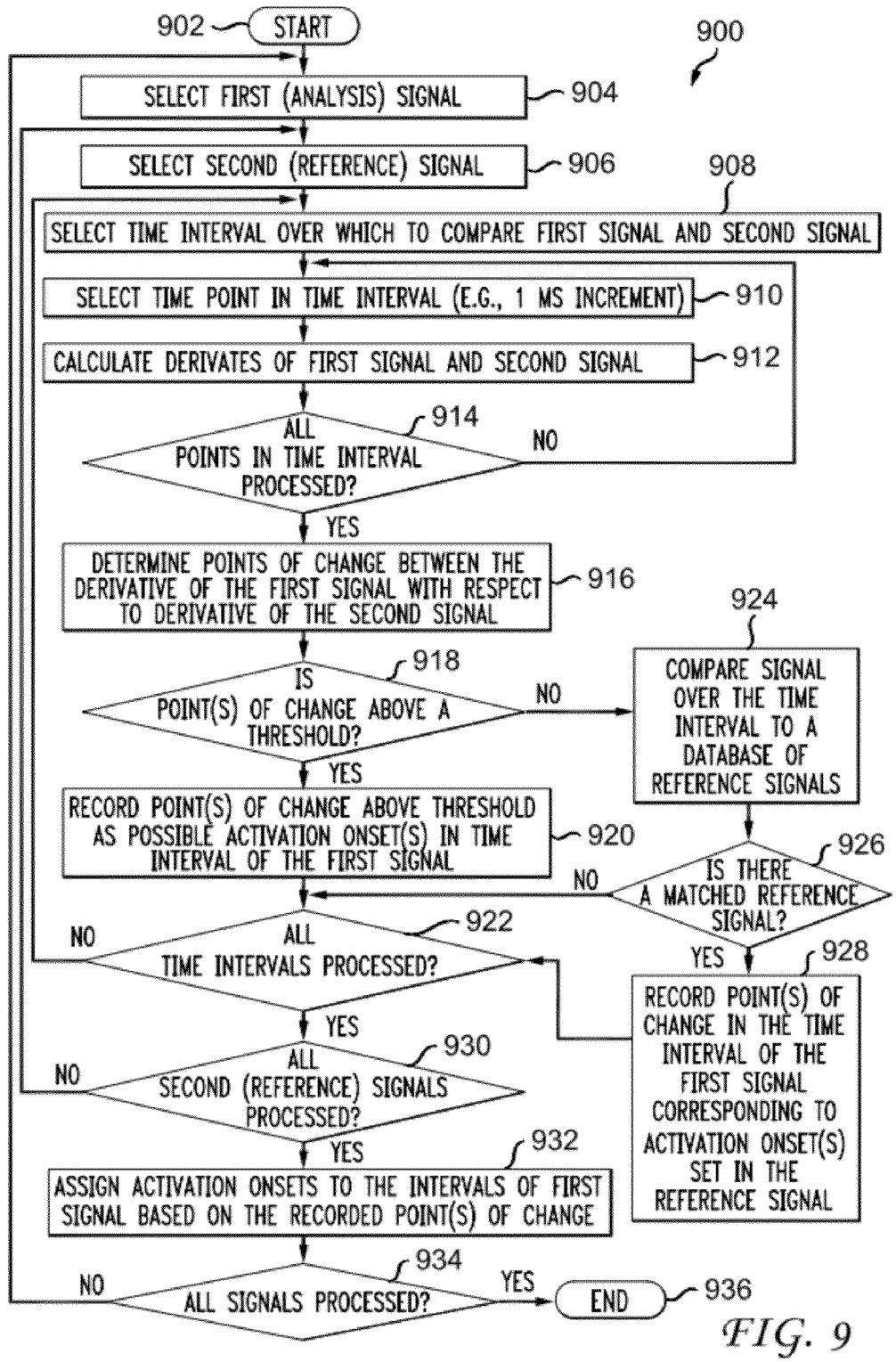
FIG. 9 is a flowchart that illustrates an example method of reconstructing cardiac activation information associated with heart rhythm disorders.

FIG. 9 is a flowchart that illustrates an example method 900 of reconstructing cardiac activation information (activation onset) associated with heart rhythm disorders. The example method 900 can be performed by the computing device 116 illustrated in FIG. 1. More specifically, the example method 900 starts at operation 902 at which signals are received by the computing device 116 via signal processing device 114 from sensors disposed in the heart 120. For example, signals can be received from sensors of the sensor array 400 disposed in the right atrium 122 of the heart 120, as shown in FIGS. 1 and 4. In some embodiments or aspects, at least a portion of the signals from the sensors can be recorded by signal processing device 114 and then provided to computing device 116.

At operation 904, a first signal (analysis signal) is selected. At operation 906, a second signal (reference signal) is selected. Selection of the analysis signal and the reference signal can be performed as described in greater detail with reference to FIGS. 4 and 5. In some embodiments or aspects, a root mean squared (RMS) can be determined for the first signal and for the second signal. At operation 908, a time interval over which the first signal and the second signal are to be compared is selected. The time interval can be selected to be an activation cycle (e.g., 100 ms to 300 ms) as described in FIG. 2. In some embodiments or aspects, the time interval can be determined by a dominant frequency analysis or other analysis of the average cycle length of the first (analysis) signal. A default time interval of 200 ms can be used if the time interval cannot be determined computationally. In other embodiments or aspects, the time interval can be selected manually, computationally by a different analysis method, from a database that catalogs such time intervals for patients of a certain age, gender and type of heart rhythm disorder, or defaulted to a value between about 100 ms and about 300 ms.

In some embodiments or aspects, a composite signal can be determined based on the selected first signal and the second signal, such as by subtracting or adding the signals as described with reference to FIG. 8.

At operation 910, a time point is selected for consideration in the selected time interval. The same or about the same time point is selected for consideration in each signal (e.g., first signal and second signal). At operation 912, derivatives are calculated for a time increment (e.g., 10 ms) extending from the point of consideration in each signal. In those embodiments or aspects that use a composite signal, a derivative is also calculated for a time increment (e.g., 10 ms) extending from a time point of consideration in the composite signal. The time point of consideration in the composite signal is the same or about the same as in the other signals (e.g., first signal and second signal).

At operation 914, a determination is made as to whether all points in the selected time interval have been processed. If it is determined that all point in the selected time interval were processed, the method 900 continues at operation 916. Alternatively, the method 900 performs operations 910, 912 until all points in the selected time interval are determined to be processed at operation 914.

At operation 916, points of change between the derivatives of the first signal with respect to the derivatives of the second signal are determined in the time interval under consideration. For example, a significance value (δ) can be determined at each point of change as described with reference to FIGS. 6-8.

At operation 918, a determination is made as to whether there is a point(s) of change in the derivative of the first cardiac signal with respect to the derivative of the second cardiac signal above a threshold. For example, it can be determined whether the significance value (δ) at the point of change is above the threshold. In some embodiments or aspects that do not use a composite signal, the threshold can be 0.25 (or another value) as described with reference to FIGS. 6-8, while in those embodiments or aspects that use a composite signal, the threshold can be computed as an average value plus a standard deviation of all points of change as described with reference to FIG. 8.

If it is determined that there is a point(s) of change above the threshold, the method 900 continues at operation 920 where the significant point(s) of change is recorded (selected) as a possible activation onset(s) for the time interval under consideration in the first (analysis) signal. If however, it is determined that there is no point of change above the threshold (no significant point of change), the method 900 continues at operation 924 where the first signal is compared over the time interval to a catalog of reference signals. For example, the catalog of reference signals for heart rhythm disorders can be maintained in database 118. At operation 926, a determination is made as to whether there is a match to a reference signal in the database. The comparison can be based on at least one characteristic of the first signal to at least one characteristic of the reference signal, such as shape, slope, amplitude, frequency and/or timing. Other characteristics can be used together with or instead of the enumerated characteristics.

If there is no match to a reference signal at operation 926, the method 900 continues at operation 922. Alternatively, the method 900 continues at operation 928 where the point(s) of change in the time interval under consideration is recorded (selected), which would correspond to activation onset(s) in the reference signal that was matched.

At operation 922, a determination is made as to whether all time intervals in the signals have been processed. If it is determined that all time intervals have not been processed, the method 900 continues to perform operations 908-922 to process subsequent time intervals until it is determined that all time intervals have been processed. The subsequent time interval can be determined from the point(s) of change that represents the possible activation onset at 920. Specifically, if only one point of change (above the threshold) is recorded at 920, then the next time interval (e.g., 100 ms to 300 ms) starts at the onset time associated with the point of change plus a half of a cycle length (e.g., 50 ms to 150 ms). If there are multiple points of change, then the onset time associated with the largest point of change (significance value) is used to determine the next time interval for operations 908-922. It is noted that the determination of the next time interval can be extended to consider significant points of change from all second (reference) signals for the same time interval under consideration. However, if it is determined that all time intervals have been processed at operation 922, the method 900 continues at operation 930.

At operation 930, a determination is made as to whether all second (reference) signals have been processed in association with the selected first (analysis) signal. If it is determined that all second signals have not been processed, the method 900 continues to perform operations 906-930 until it is determined that all second (reference) signals have been processed for the first (analysis) signal. However, if it is determined that all second signals have been processed, the method 900 continues to operation 932.

At operation 932, an activation onset(s) is assigned in the first signal at the point(s) of change to define cardiac activation(s) indicating a beat(s) in the first signal if it is determined (at operation 918) that the point(s) of change is above the threshold. Similarly, at operation 932 an activation onset(s) can be assigned in the first signal at the point(s) of change to define cardiac activation(s) indicating a beat(s) in the first signal based on a matched reference signal (at operation 928). More specifically, activation onsets are assigned to the time intervals of the first signal based on the recorded (or significant) point(s) of change of the first signal with reference to the second signal(s). That is, an activation onset is assigned to each time interval in the first (analysis) signal based possible activation onset(s) associated with the significant point(s) of change in the same time interval of the second (reference) signal(s). As described with reference to FIG. 5, the activation onset for the time interval of the first (analysis) signal can be determined based on an average of the activation onsets with reference to the second (reference) signals. In another embodiment or aspect, the activation onset for the time interval of the first signal can be determined based on an average of activation onsets with reference to those second signals in which a majority of activation onsets are within a predetermined time interval of each other (e.g., ±5 ms). The assigned onset can be recorded for each interval in the first (analysis) signal such as in database 118.

At operation 934, a determination is made as to whether all signals have been processed or analyzed as first (analysis) signals against second (reference) signals. If it is determined that all signals have not been processed, then the method 900 continues to perform operations 904-932 until all signals have been processed. Alternatively, if it is determined that all signals have been processed, the method 900 ends at operation 936.

At the conclusion of the method 900, signals collected from the heart 120 have been reconstructed with cardiac activation information (activation onsets) such that a cause of the heart rhythm disorder can be determined. More specifically, unipolar electrograms or monophasic action potentials (MAPs) can be mapped to the reconstructed activation onsets of the signals to show unipolar or MAP sequences or representations for the signals. An activation map or pattern can be constructed from these unipolar voltage or MAP voltage representations of the signals to locate the cause of the heart rhythm disorder. An example MAP representation and example activation map are illustrated in FIG. 11.

Figure 10:
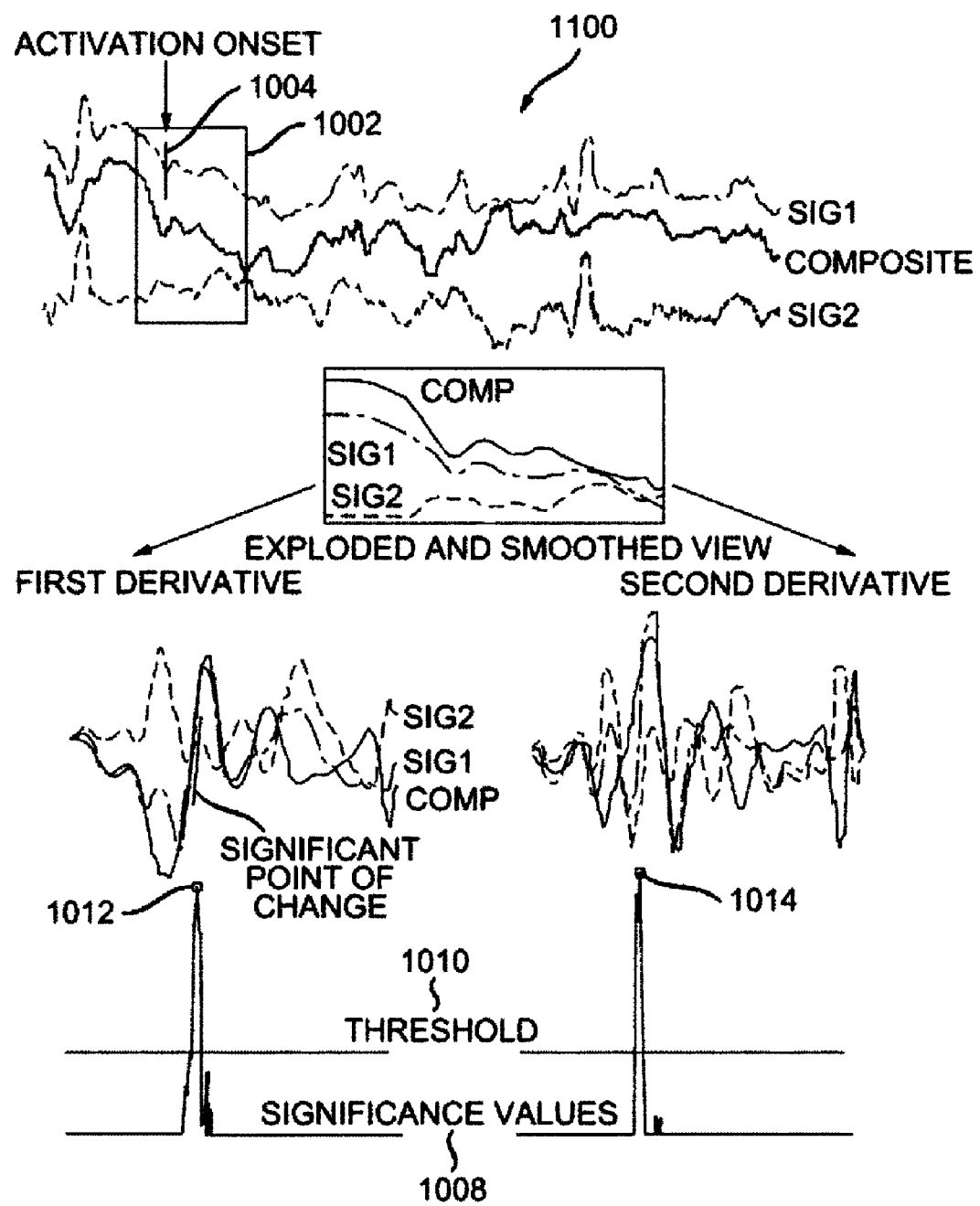
FIG. 10 is an illustration of an example signal pair comparison of analysis signal (SIG1) and reference signal (SIG2) that can be processed in accordance with the method of FIG. 9 to reconstruct cardiac activation information.

FIG. 10 is an illustration of an example signal pair comparison 1000 of analysis signal (SIG1) and reference signal (SIG2) that can be processed in accordance with method 900 of FIG. 9 to assign an activation onset 1004. As illustrated in comparison 1000, a time interval 1002 (e.g., 100 ms-300 ms) is selected for comparison and processing. In some example embodiments or aspects, the signals in the time interval (SIG1, SIG2, COMP) are smoothed, such as via median filter. Significance values (δ) are determined for the points of changes in the signals' first or second derivative, as described herein with reference to FIGS. 1-9. As illustrated in signal pair comparison 1000, point of change 1012 in SIG1 that is above threshold 1010 is assigned as the activation onset 1004 for the time interval 1002 in SIG1 based on the first derivative. Alternatively, point of change 1014 in SIG1 that is above threshold 1010 is assigned as the activation onset 1004 for the time interval 1002 in SIG1 based on the second derivative. Subsequent time intervals are selected and activation onsets are assigned as described herein with reference to FIGS. 1-9 until the analysis signal (SIG1) is processed.

Figure 11:
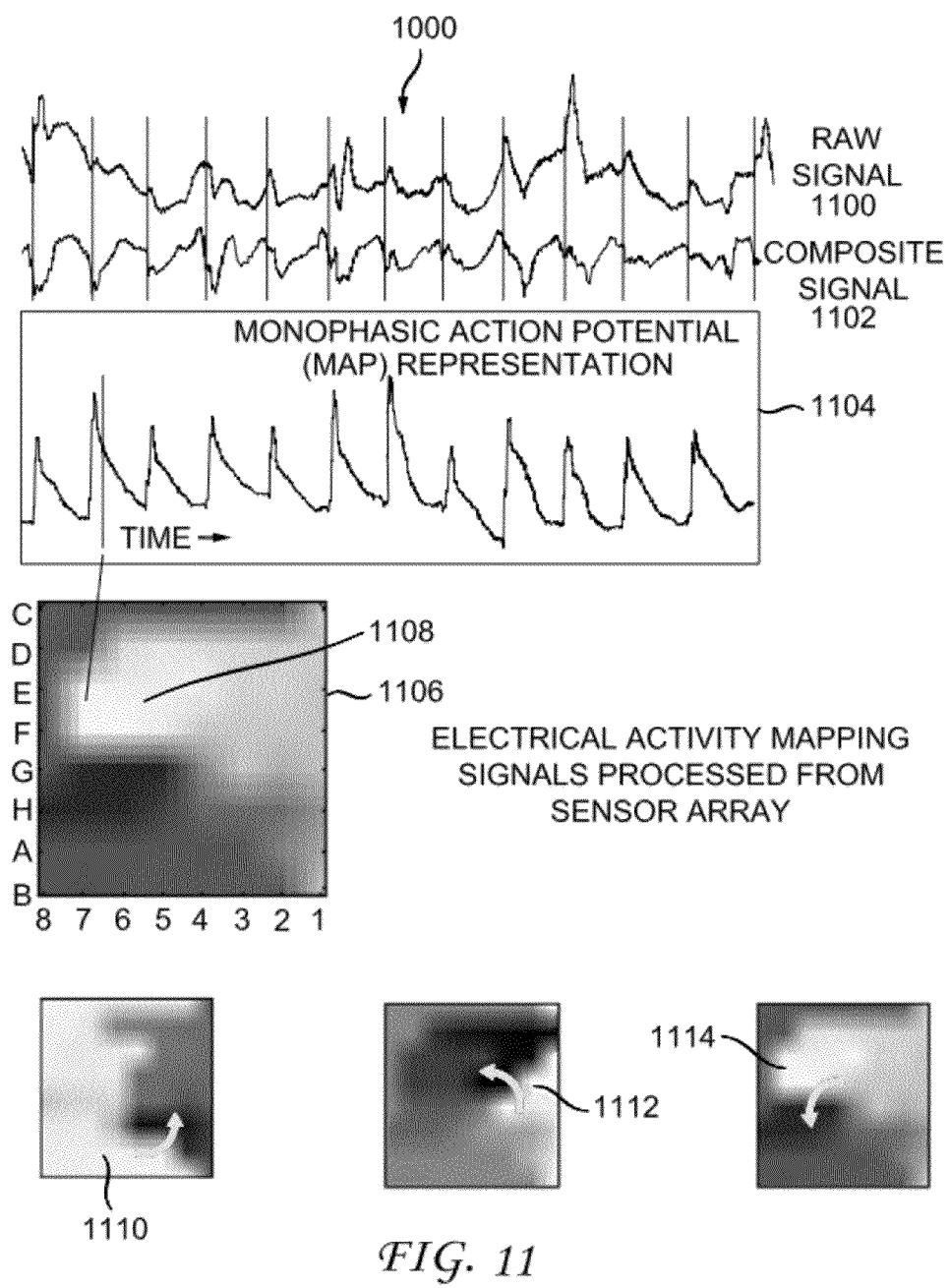
FIG. 11 is an illustration of an example mapping of processed signals in accordance with FIGS. 1-10.

FIG. 11 is an illustration of an example mapping 1100 of processed signals in accordance with FIGS. 1-10. Raw signal 1100 represents a signal that is processed to assign activation onsets (vertical lines) as described herein. For reference purposes, a composite signal 1102 is shown, which results from the raw (analysis) signal 1100 and another (reference) signal (not shown). A monophasic action potential (MAP) voltage representation is generated from for each processed signal 1100. Multiple signals are processed as described herein and MAPs generated based on the processed signals. The electrical activity of all MAPs is mapped in a sequence of example activation mappings 1106 to show activation onsets 1108, 1110, 1112 and 1114 at each time interval, respectively. These mappings can be displayed by computing device 116. Although only four mapping are shown for illustrative purposes, there can be fewer or greater number of mappings 1106 based on the time intervals represented in the signals.

As shown by the arrows in the example mappings 1106 (e.g., activation onsets 1108-1114), the electrical activity indicates a rotational activation pattern of activation onsets (rotor) in the heart rhythm disorder. At least a portion of the area of the heart 120 indicated by the rotational activation pattern indicated by the arrows in FIG. 11 can be treated to eliminate the cause of the heart rhythm disorder, and therefore the heart rhythm disorder itself. Such treatment may be delivered by ablation using various energy sources (including but not limited to radiofrequency, cryoenergy, microwave, and ultrasound), gene therapy, stem cell therapy, pacing stimulation, drug or other therapy. It is noted that the MAP representation and activation map are examples to illustrate a rotational activation pattern. Other activation patterns can result from different example signals collected by the sensors from the heart 120.

FIG. 12 is a block diagram of an illustrative embodiment of a general computer system 1200. The computer system 1200 can be the signal processing device 114 and the computing device 116 of FIG. 1. The computer system 1200 can include a set of instructions that can be executed to cause the computer system 12800 to perform any one or more of the methods or computer based functions disclosed herein. The computer system 1200, or any portion thereof, may operate as a standalone device or may be connected, e.g., using a network or other connection, to other computer systems or peripheral devices. For example, the computer system 1200 may be operatively connected to signal processing device 114 and analysis database 118.

The computer system 1200 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 1200 is illustrated, the term "system" shall also be taken to include any collection of systems or sub-systems that individually or jointly execute a set, or multiple sets, of instructions to perform one or more computer functions.

As illustrated in FIG. 12, the computer system 1200 may include a processor 1202, e.g., a central processing unit (CPU), a graphics-processing unit (GPU), or both. Moreover, the computer system 1200 may include a main memory 1204 and a static memory 1206 that can communicate with each other via a bus 1226. As shown, the computer system 1200 may further include a video display unit 1210, such as a liquid crystal display (LCD), an organic light emitting diode (OLED), a flat panel display, a solid state display, or a cathode ray tube (CRT). Additionally, the computer system 1200 may include an input device 1212, such as a keyboard, and a cursor control device 1214, such as a mouse. The computer system 1200 can also include a disk drive unit 1216, a signal generation device 1222, such as a speaker or remote control, and a network interface device 1208.

In a particular embodiment or aspect, as depicted in FIG. 12, the disk drive unit 1216 may include a computer-readable medium 1218 in which one or more sets of instructions 1220, e.g., software, can be embedded. Further, the instructions 1220 may embody one or more of the methods or logic as described herein. In a particular embodiment or aspect, the instructions 1220 may reside completely, or at least partially, within the main memory 1204, the static memory 1206, and/or within the processor 1202 during execution by the computer system 1200. The main memory 1204 and the processor 1202 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computer systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computer system processing can be constructed to implement one or more of the methods or functionality as described herein.

It is also contemplated that a computer-readable medium includes instructions 1220 or receives and executes instructions 1220 responsive to a propagated signal, so that a device connected to a network 1224 can communicate voice, video or data over the network 1224. Further, the instructions 1220 may be transmitted or received over the network 1224 via the network interface device 1208.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, system and method to reconstruct cardiac activation information have been described. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A method of reconstructing cardiac activation information comprising:
   processing a first cardiac signal and a second cardiac signal via a computing device to determine whether there is a point of change in a derivative of the first cardiac signal with respect to a derivative of the second cardiac signal above a threshold; and
   assigning an activation onset time in the first cardiac signal at the point of change to define cardiac activation indicating a beat in the first cardiac signal if it is determined that the point of change is above the threshold.

2. The method of claim 1, wherein the point of change is determined at about the same time point for the first cardiac signal and the second cardiac signal.

3. The method of claim 1, wherein the point of change is determined from one or more of slope, amplitude, timing and shape for the first cardiac signal and the second cardiac signal.

4. The method of claim 1, wherein determination of the point of change comprises:
   forming a composite cardiac signal from the first cardiac signal and the second cardiac signal;
   determining ratio values at a plurality of points in the first cardiac signal, each ratio value representing a difference between the derivative of the second cardiac signal and a derivative of the composite cardiac signal to a difference between derivative of the first cardiac signal and the derivative of the composite cardiac signal; and
   selecting as the point of change in the first cardiac signal a point having a largest ratio value from the determined ratio values.

5. The method of claim 1, wherein the threshold is higher than a noise level associated with the first cardiac signal and the second cardiac signal.

6. The method of claim 5, wherein a point of change at or below the noise level is associated with one or more signals from other regions of a heart, respiratory system, gastrointestinal tract, neurological system and electronic interference.

7. The method of claim 1, further comprising:
   matching at least one characteristic of the first cardiac signal to at least one characteristic of a reference cardiac signal in a catalog of cardiac signals if it is determined that there is no point of change above the threshold; and
   assigning an activation onset time in the first cardiac signal as an activation onset time of the reference cardiac signal to define cardiac activation indicating a beat in the first cardiac signal.

8. The method of claim 1, further comprising performing processing and assigning to define multiple cardiac activations indicating beats in the first cardiac signal.

9. The method of claim 1, further comprising iteratively selecting the first cardiac signal and the second cardiac signal from a plurality of cardiac signals.

10. The method of claim 1, further comprising:
    iteratively selecting pairs of cardiac signals from a plurality of cardiac signals, each pair having a first cardiac signal and different second cardiac signal;
    performing processing and assigning for each of the pairs to define multiple cardiac activations indicating beats for the first cardiac signal in each of the pairs; and
    reconstructing a cardiac activation pattern based on assigned activation onset times of cardiac activations from the plurality of cardiac signals to indicate a source of a cardiac rhythm disorder.

11. A system to reconstruct cardiac activation information comprising:
    at least one computing device configured to:
       process a first cardiac signal and a second cardiac signal to determine whether there is a point of change in a derivative of the first cardiac signal with respect to a derivative of the second cardiac signal above a threshold; and
       assign an activation onset time in the first cardiac signal at the point of change to define cardiac activation indicating a beat in the first cardiac signal if it is determined that the point of change is above the threshold.

12. A system of claim 11, further comprising a computer readable medium comprising instructions, which when executed by the at least one computing device, cause the at least one computing device to process and assign.

13. The system of claim 11, wherein the point of change is determined at about the same time point for both the first cardiac signal and the second cardiac signal.

14. The system of claim 11, wherein the at least one computing device is further configured to:
form a composite cardiac signal from the first cardiac signal and the second cardiac signal;
determine ratio values at a plurality of points in the first cardiac signal, each ratio value representing a difference between the derivative of the second cardiac signal and a derivative of the composite cardiac signal to a difference between the derivative of the first cardiac signal and the derivative of the composite cardiac signal; and
select as the point of change in the first cardiac signal a point having a largest ratio value from the determined ratio values.

15. The system of claim 11, wherein the at least one computing device is further configured to:
match at least one characteristic of the first cardiac signal to at least one characteristic of a reference cardiac signal in a catalog of cardiac signals if it is determined that there is no point of change above the threshold; and
assign an activation onset time in the first cardiac signal as an onset time of the reference cardiac signal to define cardiac activation indicating a beat in the first cardiac signal.

16. The system of claim 11, wherein the at least one computing device is further configured to perform processing and assigning to define multiple cardiac activations indicating beats in the first cardiac signal.

17. The system of claim 11, wherein the at least one computing device is further configured to iteratively select the first cardiac signal and the second cardiac signal from a plurality of cardiac signals.

18. The system of claim 11, further comprising a catheter with at least a first sensor and a second sensor to detect the first cardiac signal and the second cardiac signal, respectively.

19. The system of claim 11, wherein the at least one computing device is further configured to:
iteratively select pairs of cardiac signals from a plurality of cardiac signals, each pair having a first cardiac signal and different second cardiac signal;
process and assign for each of the pairs to define multiple cardiac activations indicating beats for the first cardiac signal in each of the pairs;
reconstruct a cardiac activation pattern based on assigned activation onset times of cardiac activations from the plurality of cardiac signals to indicate a source of a cardiac rhythm disorder; and
display the reconstructed cardiac activation pattern to facilitate treatment of cardiac tissue at the source to suppress, lessen or eliminate the cardiac rhythm disorder.

20. A method of treating a cardiac rhythm disorder, the method comprising:
iteratively accessing a first cardiac signal and a second cardiac signal from a plurality of cardiac signals;
processing the first cardiac signal and the second cardiac signal via a computing device to determine whether there are points of change in a derivative of the first cardiac signal with respect to a derivative of the second cardiac signal above a threshold;
assigning activation onset times to the first cardiac signal at the points of change to define cardiac activations indicating beats in the first cardiac signal if it is determined that the points of change are above the threshold;
reconstructing a cardiac activation pattern based on the assigned activation onset times to indicate a source of the cardiac rhythm disorder; and
treating cardiac tissue at the source to suppress or eliminate the cardiac rhythm disorder.

* * * * *

UNITED STATES PATENT AND TRADEMARK OFFICE
CERTIFICATE OF CORRECTION

| | |
|---|---|
| PATENT NO. | : 8,165,666 B1 |
| APPLICATION NO. | : 13/217123 |
| DATED | : April 24, 2012 |
| INVENTOR(S) | : Carey Robert Briggs et al. |

It is certified that error appears in the above-identified patent and that said Letters Patent is hereby corrected as shown below:

In the Specification

Column 1, Line 14 Under FEDERAL GRANT:
Delete entire paragraph and replace with the following:
-- This invention was made with government support under HL083359 and HL103800 awarded by the National Institutes of Health. The government has certain rights in the invention. --

Signed and Sealed this
Tenth Day of February, 2026

John A. Squires
*Director of the United States Patent and Trademark Office*